United States Patent [19]

Foreman et al.

[11] Patent Number: 4,931,447

[45] Date of Patent: Jun. 5, 1990

[54] CYCLOALKYLAMIDES OF (8β)-1-ALKYL-6-(SUBSTITUTED) ERGOLINES

[75] Inventors: Mark M. Foreman; William L. Garbrecht; Gifford P. Marzoni, all of Indianapolis; Kathleen R. Whitten, Zionsville, all of Ind.

[73] Assignee: Eli Lilly and Company, Indianapolis, Ind.

[21] Appl. No.: 394,320

[22] Filed: Aug. 14, 1989

Related U.S. Application Data

[63] Continuation of Ser. No. 62,285, Jun. 15, 1987, abandoned.

[51] Int. Cl.$^5$ .................... A61K 31/48; C07D 457/06
[52] U.S. Cl. .................................. 514/288; 514/923; 546/69
[58] Field of Search .................... 546/69; 514/288, 923

[56] References Cited

U.S. PATENT DOCUMENTS

| | | | |
|---|---|---|---|
| 2,997,470 | 8/1961 | Picoh | 546/69 |
| 3,113,133 | 12/1963 | Hofmann et al. | 260/285.5 |
| 3,183,234 | 5/1965 | Garbrecht et al. | 260/285.5 |
| 3,228,944 | 1/1966 | Bernardi et al. | 546/69 |
| 3,228,945 | 1/1966 | Camerino et al. | 546/69 |
| 4,230,859 | 10/1980 | Rucman | 546/69 |
| 4,521,421 | 6/1985 | Foreman | 514/267 |

FOREIGN PATENT DOCUMENTS

| | | | |
|---|---|---|---|
| 559586 | 4/1960 | Belgium | 546/69 |
| 717987 | 9/1965 | Canada | 546/69 |
| 789017 | 7/1968 | Canada | 546/69 |
| 125498 | 7/1967 | Czechoslovakia . | |
| 386441 | 4/1965 | Switzerland | 546/69 |
| 816273 | 7/1959 | United Kingdom | 546/69 |
| 982737 | 2/1965 | United Kingdom | 546/69 |
| 2152507 | 8/1965 | United Kingdom . | |

OTHER PUBLICATIONS

Semonsky et al, Chem. Listy 51,123 (1957).
Semonsky et al, CA 54-14287 "Ergot Alkaloids XV".
Votava et al, CA 54-4925 "Pharmacological Effects of Cyclopentylamide of d-dihydrolysergic acid".
Pioch. CA 56-3532 "Lysergic acid amides".
Semonsky et al, CA 56-3533, "Cycloalkyl-and w-cyclopentylalkylamides of D-dihydrolygeric acid".
Macek et al, CA 58-12368 "Ergot alkaloids".
Cerny et al, CA 58-501 "Ergot alkaloids XIX".
Sandoz Ltd., CA 58-557 "Lysergamides".
Bernardi et al, CA 62-4069, "Ergolines".
Westminster Bank Ltd. CA 52-11869 "Lysergic Acid Compounds".
Hofmann et al, CA 63-13341 "Lysergic Acid Compounds".
Sandoz Ltd. CA 63-14931 "Indole-nitrogen-substituted derivatives of Lygeric acid and dihydrolysergic acid".
Dorland's Ilustrated Medical Dictionary, 26th Edition, p. 626, 5-hydroxytryptamine.
Johnson et al., Journal of Medicinal Chemistry, vol. 16, No. 5, pp. 532–537 (1973).
Floss, "Biosynthesis of Ergot Alkaloids and Related Compounds", *Tetrhedron*, 32, 873 (1976).

*Primary Examiner*—Cecilia Shen
*Attorney, Agent, or Firm*—Robert A. Conrad; Leroy Whitaker

[57] ABSTRACT

This invention provides (8β)-N-cycloalkyl-1-alkyl-6-(substituted) ergoline-8-carboxamides useful for blocking 5HT$_2$ receptors in mammals having an excess of serotonin centrally or peripherally. The invention also provides methods for treating hypertension, migraine, vasospasm, thrombosis, ischemia, depression, anxiety, sleep disorders and appetite disorders with a compound of the invention.

44 Claims, No Drawings

CYCLOALKYLAMIDES OF (8β)-1-ALKYL-6-(SUBSTITUTED) ERGOLINES

This application is a continuation of Ser. No. 07/062,285, filed on June 15, 1987 now abandoned.

SUMMARY OF THE INVENTION

The present invention relates to a compound of the formula

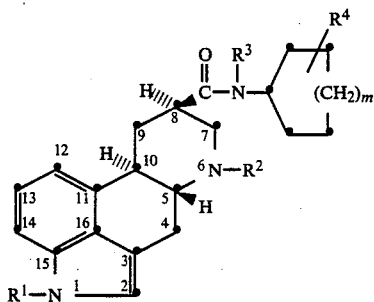

wherein:
$R^1$ is $C_1$-$C_4$ alkyl;
$R^2$ is allyl or $C_1$-$C_4$ straight chain alkyl;
$R^3$ is hydrogen or $C_1$-$C_4$ straight chain alkyl;
$R^4$ is hydrogen, $C_1$-$C_4$ alkyl, hydroxy or $C_1$-$C_4$ alkoxy;
m is 0, 1, 2 or 3; and
the pharmaceutically acceptable acid addition salts thereof.

The present invention also provides pharmaceutical formulations comprising, and methods of using, compounds of the invention.

DETAILED DESCRIPTION OF THE INVENTION

In the above formula, the term "$C_1$-$C_4$ alkyl" represents a straight or branched alkyl chain having from one to four carbon atoms. Typical $C_1$-$C_4$ alkyl groups include methyl, ethyl, n-propyl, isopropyl, n-butyl, sec-butyl and the like.

$C_1$-$C_4$ Straight chain alkyl represents a straight, but not branched, alkyl chain having from one to four carbon atoms. $C_1$-$C_4$ Straight chain alkyl groups are methyl, ethyl, n-propyl and n-butyl.

$C_1$-$C_4$ Alkoxy represents a straight or branched alkoxy chain having from one to four carbon atoms. Typical $C_1$-$C_4$ alkoxy groups include methoxy, ethoxy, n-propoxy, isopropoxy, n-butoxy and the like.

When m is 0, the ring attached to the amide nitrogen atom is cyclopentyl; when m is 1, the ring is cyclohexyl; when m is 2, the ring is cycloheptyl; and when m is 3, the ring is cyclooctyl. If the cycloaklkyl ring is substituted, the substituent may be at any available position on the ring.

While all of the compounds of the present invention are believed useful for blocking 5HT$_2$ receptors in mammals, certain of the compounds are preferred for such use. Preferably, $R^1$ is isopropyl. Also, $R^2$ is preferably methyl, $R^3$ is hydrogen, and m is 1. $R^4$ is preferably hydrogen. Other preferred aspects of the present invention will be noted hereinafter.

Compounds of the present invention are named as ergoline derivatives in which the trans(−) or 5R,10R configuration of the bridgehead hydrogens is specified. This is the same configuration as in the naturally-occurring 9,10-dihydro ergot alkaloids. In U.S. Pat. No. 3,580,916, a different naming system is used. The basic ring system is named as a 6aR,10aR-4,6,6a,7,8,9,10,10a-octahydroindolo[4,3-f,g]-quinoline. Illustratively, by the alternating naming system, 9,10-dihydrolysergic acid becomes 6aR,10aR-7-methyl-4,6,6a,7,8,9,10,10a-octahydroindolo[4,3-f,g]-quinoline-9β-carboxylic acid. Another equally valid name for dihydrolysergic acid is (8β)-6-methylergoline-8-carboxylic acid. The trivial name "ergoline" will be employed herein with the numbering system specified above for compounds of the invention.

While the configuration at asymmetric carbons 5,8 and 10 in the above formula as set as 5β,8β and 10α, generally speaking, the substituted cycloalkyl amide group contains two additional asymmetric carbons. For example, 3-methoxycyclohexylamide exists as two racemates, each racemate containing two enantiomers or stereoisomers. However, where the substituted cycloalkylamide possesses a plane of symmetry, mirror images turn out to be superimposable, and the compound actually exists in only two forms. These forms are designated as the cis form and the trans form, drawn for convenience in two dimensions as Ia and Ib.

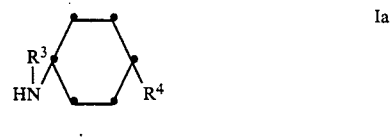

cis

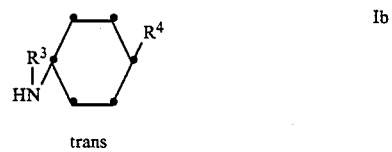

trans

When amide of a (8β)-6-methylergoline-8-carboxylic acid is formed with a cis or trans 4-substituted cycloalkyl amine, the product will be a single geometrical isomer. In general, the two amides in this instance will also be named, for the sake of simplicity, as cis and trans (4-substituted)cycloalkyl amides. This invention contemplates all such forms useful for blocking 5HT$_2$ receptors in mammals; that is, the individual diastereoisomers and geometrical isomers as well as racemates.

Pharmaceutically-acceptable acid addition salts of the compounds of the invention include salts derived from non-toxic inorganic acids such as hydrochloric acid, nitric acid, phosphoric acid, sulfuric acid, hydrobromic acid, hydriodic acid, phosphorous acid and the like, as well as salts derived from non-toxic organic acids such as aliphatic mono- and dicarboxylic acids, phenyl-substituted alkanoic acids, alkandioic acids, aromatic acids, aliphatic and aromatic sulfonic acids, and the like. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalene-1-sulfonate, naphthalene-2-sulfonate and like salts.

The following examples further illustrate specific compounds of the present invention:

(8β)-N-Cyclohexyl-1-isopropyl-6-n-butyl-ergoline-8-carboxamide (8β)-N-(3-Methylcyclopentyl)-1-sec.-butyl-6-methylergoline-8-carboxamide maleate (8β)-N-Cycloheptyl-1,6-diethylergoline-8-carboxamide nitrate (8β)-N-Cyclohexyl-N-ethyl-1-isopropyl-6-methylergoline-8-carboxamide (8β)-trans-N-(4-Methoxycyclooctyl)-1-isopropyl-6-methylergoline-8-carboxamide hydrochloride (8β)-N-Cycloheptyl-N-methyl-1-isopropyl-6-n-propylergoline-8-carboxamide (8β)-N-Cyclohexyl-1-t-butyl-6-n-propylergoline-8-carboxamide (8β)-N-Cyclohexyl-1-t-butyl-6-methylergoline-8-carboxamide succinate (8β)-cis-N-(4-Methylcyclohexyl)-1-ethyl-6-methylergoline-8-carboxamide citrate (8β)-N-Cyclopentyl-1-sec.-butyl-6-methylergoline-8-carboxamide lactate (8β)-N-Cyclohexyl)-N-n-propyl-1-isopropyl-6-methylergoline-8-carboxamide (8β-N-Cyclopentyl-N-methyl-1-n-butyl-6-n-butylergoline-8-carboxamide (8β)-N-Cyclohexyl-1-isopropyl-6-n-allylergoline-8-carboxamide acetate (8β)-N-Cyclooctyl-1-isopropyl-6-methylergoline-8-carboxamide (8β)-N-Cycloheptyl-1-n-propyl-6-methylergoline-8-carboxamide maleate (8β)-N-Cyclohexyl-1,6-di(n-propyl)ergoline-8-carboxamide (8β)-N-Cyclopentyl-N-methyl-1,6-dimethylergoline-8-carboxamide (8β)-cis-N-(4-Hydroxycycloheptyl)-1,6-diethylergoline-8-carboxamide (8β)-N-Cyclopentyl-1-isopropyl-6-ethylergoline-8-carboxamide hydrobromide (8β)-N-(4-Hydroxycyclohexyl)-1-n-butyl-6-methylergoline-8-carboxamide malonate (8β)-N-Cyclohexyl-1-n-butyl-6-n-propylergoline-8-carboxamide (8β)-N-Cycloheptyl-1-n-butyl-6-methylergoline-8-carboxamide (8β)-N-(4-Methylcyclohexyl)-N-methyl-1-n-propyl-6-methylergoline-8-carboxamide malate (8β)-N-(3-Methylcyclooctyl)-N-methyl-1-isopropyl-6-allylergoline-8-carboxamide (8β)-N-Cyclooctyl-1-sec.-butyl-6-methylergoline-8-carboxamide tartrate (8≠)-N-(4-Methoxycyclohexyl)-1-isopropyl-6-n-butylergoline-8-carboxamide (8β)-N-Cycloheptyl-1-methyl-6-methylergoline-8-carboxamide oxalate (8β)-cis-N-(4-Hydroxycyclohexyl)-N-n-propyl-1-methyl-6-n-propylergoline-8-carboxamide (8β)-N-Cyclopentyl-1-t-butyl-6-methylergoline-8-carboxamide (8β)-N-Cyclohexyl-1,6-diethylergoline-8-carboxamide (8β)-N-(3-Methylcyclohexyl)-1-isopropyl-6-n-propylergoline-8-carboxamide maleate (8β)-N-(4-Methylcyclooctyl)-1-isopropyl-6-methylergoline-8-carboxamide suberate (8β)-N-(3-Methoxycyclohexyl)-1-n-propyl-6-allylergoline-8-carboxamide (8β)-N-Cycloheptyl-N-methyl-1-n-butyl-6-methylergoline-8-carboxamide citrate (8β)-N-Cyclohexyl-N-n-butyl-1-isopropyl-6-methylergoline-8-carboxamide (8β)-N-(4-Methylcyclopentyl)-N-ethyl-1-isopropyl-6-methylergoline-8-carboxamide hydroiodide The compounds of the present invention may be prepared by a variety of procedures well known to those of ordinary skill in the art. Preferably, for compounds wherein $R^2$ is methyl, dihydrolysergic acid is converted to the alkali metal salt and then to the $(C_1-C_4$ alkyl)-formate derivative. This compound is finally reacted with the appropriate cycloalkylamine to provide a compound of the invention. This reaction is represented by the following scheme:

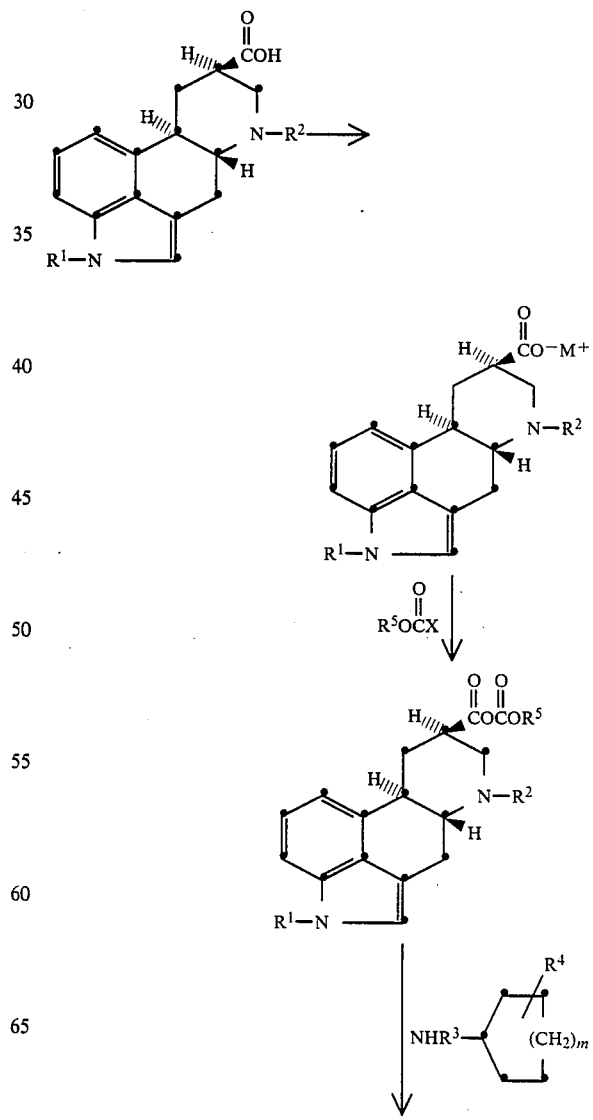

-continued

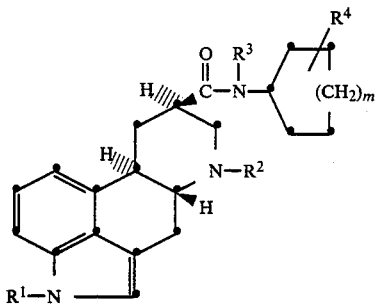

wherein $R^1$, $R^2$, $R^3$, $R^4$ and m are as defined above, $R^5$ is $C_1$–$C_4$ alkyl, such as methyl, ethyl or preferably isobutyl, X is halogen, especially chloro, and M is an alkali metal.

The reaction can be carried out by combining the dihydrolysergic acid derivative with about an equimolar quantity to slight excess of the base containing an alkali metal in a mutual solvent such tetrahydrofuran, diethyl ether, dichloromethane, dioxane, dimethylsulfoxide, N,N-dimethylformamide (DMF), benzene, toluene, and the like. Commonly used bases include sodium or potassium hydride, sodium carbonate and especially potassium carbonate. This mixture is typically heated to form the alkali metal salt intermediate. The mixture is next cooled and an equimolar to slight excess of a $C_1$–$C_4$ alkyl haloformate is added to the reaction mixture. After sufficient time to form the ($C_1$–$C_4$ alkyl)formate intermediate, typically approximately five to about 30 minutes, at least one equivalent of the desired cycloalkylamine is added to the reaction mixture. Generally, the reaction is substantially complete after about two to about 200 hours when carried out at a temperature of about −40° to about 50° C., preferably from about −20° to about 25° C. The product of the reaction may be isolated by simply removing the reaction solvent, for instance by evaporation under reduced pressure. More typically, the reaction mixture containing the free base of the desired compound may be combined with water, and the product collected by filtration or extracted into a water immiscible solvent. The product thus isolated can be further purified if desired by any of several well known techniques.

If the desired final product is not a 9,10-dihydrolysergic acid amide, that is, not a (8β)-6-methylergoline-8-carboxamide, but is a 6-ethyl, 6-n-propyl, 6-n-butyl, or the like derivative, the replacement of the 6-methyl group must take place prior to the amidation procedure described above. In this procedure, it is preferable to use a lower alkyl (such as methyl or ethyl) ester of a 9,10-dihydrolysergic acid. Replacement of the 6-methyl group with ethyl, n-propyl, n-butyl, or the like, can be carried out by the procedure of Kornfeld and Bach, U.S. Pat. No. 4,166,182, whereby the N-methyl group is reacted with cyanogen bromide to form an N-cyano derivative. The cyano group can be removed by hydrogenation using zinc dust and hydrochloric acid. Alternatively, basic hydrolysis can be used. Either procedure provides a secondary amine group at the 6-position, but also a free 8β-carboxylic acid since the hydrolysis also saponifies the 8β-lower alkyl ester group. Next, the 6-position is alkylated or allylated under standard conditions followed by amidation with the desired cycloalkylamine. This procedure is graphically illustrated by the following reaction scheme:

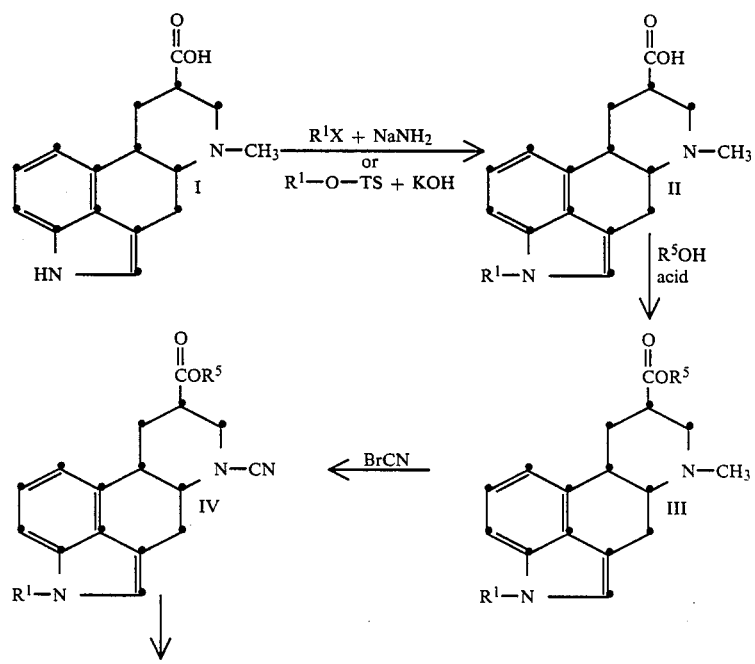

-continued

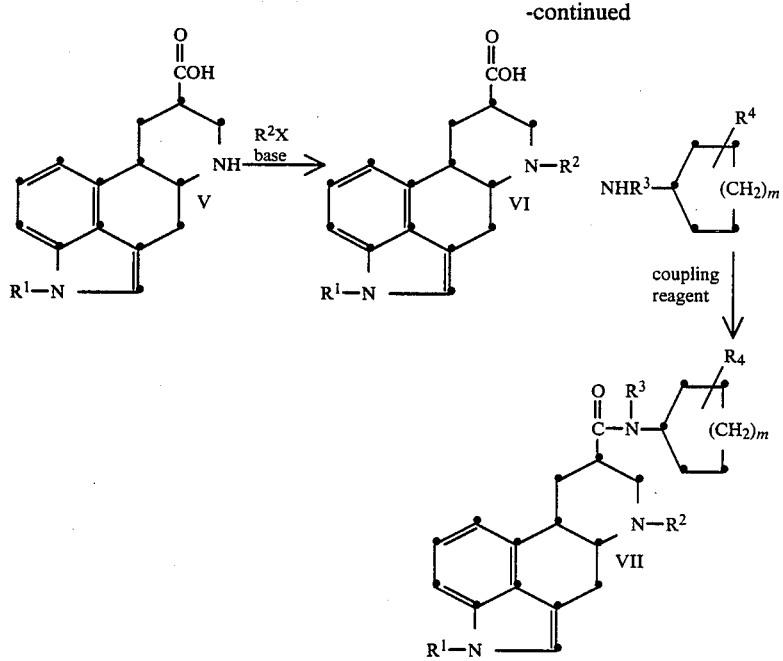

wherein $R^1$, $R^2$, $R^3$, $R^4$ and m are as defined above, $R^5$ is $C_1$–$C_4$ alkyl and X is a good leaving group such as halo or a sulfonate derivative.

More specifically, in the above reaction scheme, 9,10-dihydrolysergic acid (1) is alkylated on the indole nitrogen with a primary or secondary $C_1$–$C_4$ alkyl halide using sodamide to create the reactive anion, or preferably using an aryl sulfonate such as a p-tosylate in the presence of potassium hydroxide in DMSO. The N-1 product (11) is then esterified with a lower alkanol $R^5OH$ (a $C_1$–$C_2$ alkanol preferably) to yield the ester (111). This intermediate is then reacted with BrCN by standard procedures to replace the methyl group and form a 6-cyano derivative (IV). Removal of the cyano group under the preferred basic conditions yields a (8β)-6-ergoline-8-carboxylic acid (V). The ring nitrogen at $N^6$ is then realkylated with a $C_1$–$C_4$ alkyl halide or allyl halide in the presence of base under standard conditions. Finally, the acid is converted to the amide with a desired cycloalkylamine by the procedures herein described, such as with a coupling reagent such as N,N'-dicyclohexylcarbodiimide or carbonyldiimidazole to yield the compounds of this invention (VII).

It might seem redundant to realkylate at $N^6$ with a methyl group since that group is present in the 9,10-dihydrolysergic acid starting material. However, the process would enable one to insert a "tagged" ($C^{14}$ or $H^3$) methyl group into the compound for metabolic studies.

The compounds of the present invention may also be prepared by the reaction of a 1-alkyl-6-(substituted)ergoline-8-hydrazide with the desired cycloalkylamine under conditions well known to those of ordinary skill in the art. This reaction may be represented by the following scheme:

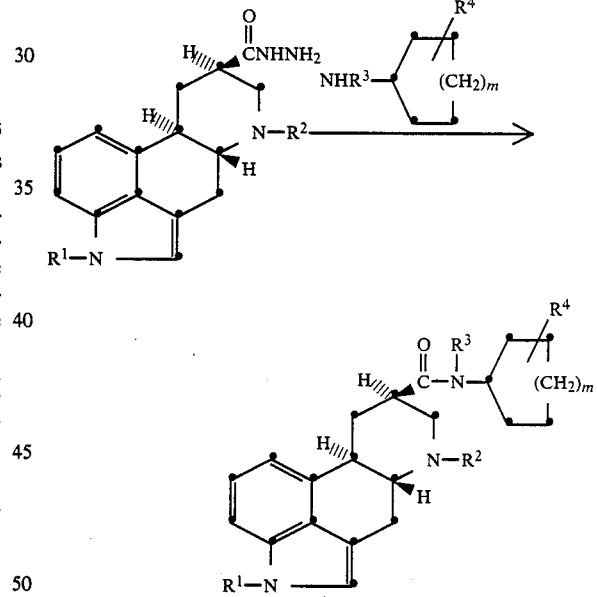

wherein $R^1$, $R^2$, $R^3$, $R^4$ and m are as defined above.

According to this procedure, the hydrazide starting material is dissolved in an aqueous acidic solution and the resulting mixture is cooled to a temperature in the range of about 0° C. to about 20° C. Typical acids suitable for use in this step of the process include the hydrohalic acids, such as hydrobromic acid and hydroiodic acid, and especially hydrochloric acid. To this mixture is added either sodium nitrite or sodium periodate, typically in an excess amount, and the mixture is made basic with a suitable base such as the inorganic bases, especially sodium bicarbonate. The intermediate formed by this reaction is isolated by extraction with a water immisible organic solvent, and an equimolar, to preferably an excess, of the desired cycloalkylamine is combined with the solution containing the intermediate. The reaction is substantially complete within about one to 24 hours when conducted at a temperature in the range of about 0° C. to about 100° C., more preferably within about four to 12 hours when conducted at a temperature in the range of about 5° C. to about 20° C. The product is then isolated, typically by decanting or evaporating the volatile constituents under vacuum. The isolated product may then be further purified, if desired, by standard procedures.

The compounds of the present invention may also be prepared by the direct coupling of a (8β)-1-alkyl-6-(substituted)ergoline-8-carboxylic acid derivative with an appropriate cycloalkylamine in the presence of a coupling reagent to provide the corresponding (8β)1-alkyl-6-(substituted)ergoline-8-carboxamide. This reaction may be represented by the following scheme:

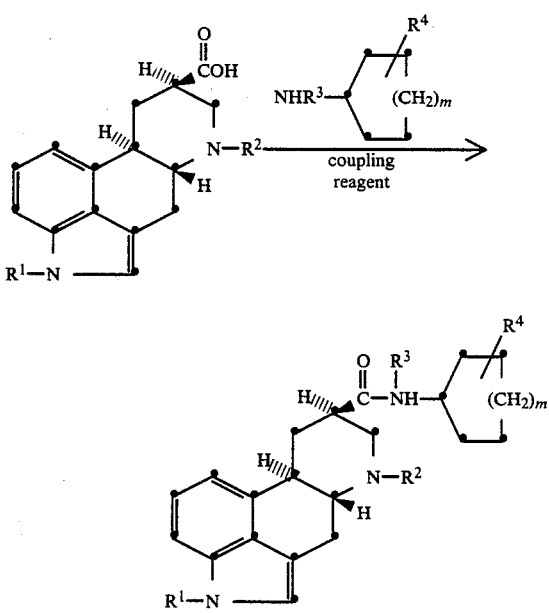

wherein $R^1$, $R^2$, $R^3$, $R^4$ and m are as defined above.

This reaction process necessitates the use of a coupling reagent, for example any of the type of coupling reagents commonly employed in the synthesis of peptides. Examples of such coupling reagents include the carbodiimides such as N,N'-dicyclohexylcarbodiimide, N,N'-diisopropylcarbodiimide, or N,N'-diethylcarbodiimide; the imidazoles such as carbonyldiimidazole; as well as reagents such as 1-hydroxybenzotriazole mesylate or N-ethoxycarbonyl-2-ethoxy-1,2-dihydroquinoline (EEDQ). The direct coupling of a (8β)-1-alkyl-6-(substituted)-ergoline-8-carboxylic acid and a cycloalkylamine is carried out by adding about an equimolar quantity of the amine starting material to a solution of the carboxylic acid in the presence of an equimolar quantity to slight excess of the coupling reagent. The reaction generally is carried out in an unreactive organic solvent such as dichloromethane, tetrahydrofuran (THF) or N,N-dimethylformamide (DMF), and is typically complete within about twenty-four hours when conducted at a temperature of about 0° to about 30° C. The product is then typically isolated by filtration. The (8β)-1-alkyl-6-(substituted)ergoline-8-carboxamide thus formed can be further purified, if needed, by any of several routine methods, including crystallization from common solvents, chromatography over solid supports such as silica or alumina, and related purification techniques.

The preparation of the ergoline compounds which are intermediates to the compounds of the present invention is well known to those of ordinary skill in the art. According to this procedure, dihydrolysergic acid is first alkylated on the N-1 nitrogen atom with an alkyl halide in the presence of base. Liquid ammonia is a convenient solvent with sodamide as the preferred base. An alternate alkylation procedure whereby a sulfonate derivative is used in the presence of an alkali metal hydroxide is more fully described in the pending U.S. application Ser. No. 782,339, of Marzoni, filed Oct. 1, 1985. According to this procedure, an arylsulfonate of the structure R-O-SO$_2$-phenyl-Y, wherein Y is H, 4-CH$_3$, 4-Br or 4-NO$_2$ is reacted with an ergoline-8-carboxylic acid in a suitable solvent, conveniently DMSO, in the presence of base, preferably sodium or potassium hydroxide.

To synthesize compounds wherein the 6-position is other than methyl, that is, the compound possesses a 6-ethyl, 6-n-propyl, 6-n-butyl substituent, or the like derivative, the replacement of the 6-methyl group will take place prior to the final amidation as described above.

The pharmaceutically acceptable acid addition salts of the invention are typically formed by reacting an amine of the invention with an equimolar or excess amount of acid. The reactants are generally combined in a mutual solvent such as diethyl ether or benzene, and the salt normally precipitates out of solution within about one hour to 10 days, and can be isolated by filtration.

The following Examples further illustrate the compounds of the present invention and methods of their synthesis. The Examples are not intended to be limiting to the scope of the invention in any respect and should not be so construed.

EXAMPLE 1

(8β)-N-Cyclohexyl-1-isopropyl-6-methylergoline-8-carboxamide

To a 250 ml three-neck round bottom flask was added 10.0 g (32.01 mmol) of (8β)-1-isopropyl-6-methyl ergoline-8-carboxylic acid, 4.43 g (32.1 mmol) of potassium carbonate and 200 ml of N,N-dimethylformamide. The mixture was refluxed and 25 ml of a distillate was collected. The remaining solution was cooled in an ice bath, and then with an acetonitrile/carbon dioxide bath which lowered the temperature of the reaction mixture to about −45° C. To this mixture was added 4.59 g (33.62 mmol) of isobutyl chloroformate dropwise. The resulting mixture was stirred for approximately five minutes and 3.49 g (35.21 mmol) of cyclohexylamine was added. The reaction mixture was allowed to warm to room temperature and stirred for approximately 19 hours. To the mixture was added 500 ml of ice water containing 25 ml of concentrated ammonium hydroxide. The mixture was cooled and the precipitated solid was collected by vacuum filtration. The resulting solid was washed with water and dried in vacuo to provide 10.13 g of the title compound having a purity of 92.3%. Yield 76.8%.

The resulting solid was combined with three other lots of the desired compound previously synthesized to provide a total weight of 33.6 g. This material was dissolved in 1200 ml of hot methanol and the resulting solution was filtered. The filtrate was allowed to cool to room temperature and 600 ml of water was added dropwise. The mixture was cooled in the freezer and the precipitated crystals were collected by vacuum filtration. The crystals were washed with methanol and dried in vacuo to provide 26.95 g of the desired compound having a purity of 96.5% as determined by HPLC. The dried solid was dissolved in 1100 ml of hot methanol, and the resulting solution was filtered hot and allowed to cool. To this mixture was added 600 ml of water and again the precipitated solid was collected by vacuum filtration. The solid was washed with water and dried in vacuo to provide 25.82 g of the title compound. The assayed material indicated 98.7% purity. mp>250° C.

Analysis calculated for $C_{25}H_{35}N_3O$: Theory: C, 76.29; H, 8.96; N, 10.68; Found: C, 76.26; H, 8.75; N, 10.50.

m/e=393 $[\alpha]_D^{25}= -83.6931$.

Following the general procedure set forth in Example 1, the compounds of Examples 2 and 3 were synthesized.

EXAMPLE 2

(8β-N-Cyclohexyl-N-methyl-1-isopropyl-6-methylergoline-8-carboxamide maleate, mp=149°-154° C.

Analysis calculated for $C_{30}H_{41}N_3O_5$: Theory: C, 68.81; H, 7.89; N, 8.02; Found: C, 68.62; H, 7.61; N, 7.81.

m/e=407 $[\alpha]_D^{25}= -76.0396$.

EXAMPLE 3

(8β)-N-Cyclohexyl-1-isopropyl-6-n-propylergoline-8-carboxamide, mp=235°-237° C.

Analysis calculated for $C_{27}H_{39}N_3O$: Theory: C, 76.92; H, 9.32; N, 9.96; Found: C, 76.85; H, 9.50; N, 9.97.

m/e=421 $[\alpha]_D^{25}=76.7791$.

EXAMPLE 4

(8β)-cis-N-(4-Methoxycyclohexyl)-1-isopropyl-methylergoline-8-carboxamide

A 50 ml three-neck round bottom flask was charged with 1.71 g (5.49 mmol) of (8β)-1-isopropyl-6-methylergoline-8-carboxylic acid, 1.52 g (11.01 mmol) of potassium carbonate and 25 ml of N,N-dimethylformamide. The mixture was refluxed and 3 ml of a distillate was collected. The mixture was cooled to room temperature and then to approximately −38° C. with an acetonitrile/carbon dioxide external cooling bath. To the mixture was added 0.79 g (5.76 mmol) of isobutyl chloroformate in one portion. The mixture was stirred for approximately ten minutes and 1.0 g (6.03 mmol) of cis-4-methoxycyclohexylamine hydrochloride was added to the reaction mixture. The mixture was stirred at −35° C. for 3 hours and 100 ml of water containing 10 ml of ammonium hydroxide was added. The precipitated solid was collected by a vacuum filtration and washed with water. The solvent was dried in vacuo to provide 1.9 g of the desired product having a purity of 99.5%. mp=220°-221° C.

Analysis calculated for $C_{26}H_{37}N_3O_2$: Theory: C, 73.72; H, 8.80; N, 9.92; Found: C, 73.49; H, 8.60; N, 9.70.

m/e=423 $[\alpha]_D^{25}=81.8546$.

EXAMPLE 5

(8β)-trans-N-(4-Methoxycyclohexyl)-1-isopropyl-6-methylergoline-8-carboxamide

Following the general procedure described in Example 4, 2.32 g of the title compound was prepared employing 1.71 g (5.49 mmol) of (8β)-1-isopropyl-6-methylergoline-8-carboxylic acid and 1.0 g (6.03 mmol) of trans-4-methoxycyclohexylamine. mp>230° C.

Analysis calculated for $C_{26}H_{37}N_3O_2$: Theory: C, 73.72; H, 8.80; N, 9.92; Found: C, 73.97; H, 8.59; N, 9.93.

m/e=423 $[\alpha]_D^{25}= -79.6284$.

Following the general procedure set forth in Example 4, the compounds of Examples 6-8 were prepared.

EXAMPLE 6

(8β)-cis-N-(4-Methoxycyclohexyl)-1,6-dimethylergoline-8-carboxamide maleate, mp=144°-146° C.

Analysis calculated for $C_{28}H_{37}N_3O_6$: Theory: C, 65.73; H, 7.29; N, 8.21; Found: C, 65.46; H, 7.27; N, 8.05.

EXAMPLE 7

(8β)-cis-N-(4-Methoxycyclohexyl)-1-ethyl-6-methylergoline-8-carboxamide maleate, mp=133°-136° C.

Analysis calculated for $C_{29}H_{39}N_3O_6$: Theory: C, 66.26; H, 7.48; N, 7.99; Found: C, 66.49; H, 7.50; N, 8.16.

EXAMPLE 8

(8β)-N-Cyclohexyl-1,6-dimethylergoline-8carboxamide, mp=260°-261.5° C.

Analysis calculated for $C_{23}H_{31}N_3O$:
Theory: C, 75.58; H, 8.55; N, 11.50;
Found: C, 75.72; H, 8.73; N, 11.75.

EXAMPLE 9

(8β)-N-Cyclopentyl-1-isopropyl-6-methylergoline-8-carboxamide

To a solution of 3.26 g (0.01 mol) of (8β)-1-isopropyl-6-methylergoline-8-hydrazide dissolved in 25 ml of hydrochloric acid and 100 ml of water at a temperature of about 5° C. was added 55 ml of a solution of 0.2N sodium nitrite dropwise over a period of about five minutes. The resulting mixture was stirred at room temperature for approximately five minutes and sufficient saturated sodium bicarbonate solution was added dropwise until the pH of the mixture was basic. The mixture was extracted with three 200 ml portions of diethyl ether. The organic extracts were combined, dried over anhydrous magnesium sulfate and filtered. To the resulting filtrate was added a solution of 2.55 g (0.03 mol) of cyclopentylamine dissolved in 50 ml of DMF. The resulting mixture was stored at a temperature of about 5° C. overnight. The solvent was decanted from the resulting oil. The oil was slurried in acetonitrile and the solvent was again decanted. The resulting solid was recrystallized from acetonitrile to provide 1.23 g of the desired compound. m/e=379.

Analysis calculated for $C_{24}H_{33}N_3O$: Theory: C, 75.95; H, 8.76; N, 11.09; Found: C, 76.21; H, 8.54; N, 10.68.

Following the general procedure of Example 9, the compound of Example 10 was synthesized.

EXAMPLE 10

(8β)-N-Cyclohexyl-1-ethyl-6-methylergoline-8-carboxamide, m/e=379

Analysis calculated for $C_{24}H_{33}N_3O$: Theory: C, 75.55; H, 8.76; N, 11.07; Found: C, 75.68; H, 8.46; N, 10.98.

EXAMPLE 11

(8β)-trans-N-(4-Hydroxycyclohexyl)-1-isopropyl-methylergoline-8-carboxamide

A mixture of 3.12 g (0.01 mol) of (8β)-1-isopropyl-6-methylergoline-8-carboxylic acid, 6.0 g (0.04 mol) of 4-aminocyclohexanol hydrochloride, 4.44 g (6.0 ml, 0.04 mol) of triethylamine and 3.0 g (0.012 mol) of EEDQ in 100 ml of dichloroethane was heated at about 72° C. for about four hours. The mixture was cooled and an aqueous solution at pH 10 was added. The organic phase was separated, and concentrated under vacuum. The resulting residue was slurried in hot acetonitrile and the undissolved solid was collected by vacuum filtration. The collected solid was recrystallized from a solvent mixture of 75 ml of methanol and 45 ml of water to provide 1.18 g of the title compound. m/e=409.

Analysis calculated for $C_{25}H_{35}N_3O_2$: Theory: C, 73.31; H, 8.61; N, 10.26; Found: C, 73.58; H, 8.71; N, 10.41.

Following the general procedure of Example 11, compounds of Examples 12–14 were synthesized.

EXAMPLE 12

(8β)-N-Cycloheptyl-1-isopropyl-6-methylergoline-8-carboxamide, m/e=407

Analysis calculated for $C_{26}H_{37}N_3O$: Theory: C, 76.62; H, 9.15; N, 10.31; Found: C, 76.48; H, 8.85; N, 10.23.

EXAMPLE 13

(8β)-N-(4-Methylcyclohexyl)-1-isopropyl-6-methylergoline-8-carboxamide, m/e=407

Analysis calculated for $C_{26}H_{37}N_3O$: Theory: C, 76.62; H, 9.15; N, 10.31;
Found: C, 76.37; H, 8.91; N, 10.16.

EXAMPLE 14

(8β)-N-(2-Hydroxycyclohexyl)-1-isopropyl-6-methylergoline-8-carboxamide, m/e=409

Analysis calculated for $C_{25}H_{35}N_3O_2$: Theory: C, 73.31; H, 8.61; N, 10.26;
Found: C, 73.09; H, 8.45; N, 10.04.

As noted above, the compounds of the present invention are useful for blocking $5HT_2$ receptors in mammals having an excess of serotonin centrally or peripherally. As such, this invention also provides a method of blocking $5HT_2$ receptors which comprises administering to a mammal having an excess of serotonin centrally or peripherally a $5HT_2$ blocking dose of a compound of the invention. This method is potentially useful in treating disease states in which an excess of circulating serotonin is a major contributing cause. These disease states include hypertension, thrombosis, migraine, vasospasm (both coronary and cerebral), ischemia, depression, anxiety, sleep disorders and appetite disorders.

The compounds of the invention show relatively slight affinity for other receptors such as $\alpha_1$, $\alpha_2$, $\beta$, histamine, carbachol and the like receptors, and thus are highly selective in their action. In mammals, hypertension may be mediated through $5HT_2$ receptors. Thus, compounds of the invention will lower blood pressure in humans as does ketanserin, another $5HT_2$ blocker, but without the side effects attributable to alpha adrenergic receptor blockade of ketanserin.

In carrying out the methods of the invention, a compound of the invention is administered orally or parenterally to a mammal with an excess of circulatory serotonin in which mammal it is desirable to block $5HT_2$ receptors in order to alleviate symptoms attributable to excessive serotonin levels such as high blood pressure and migraine. For parenteral administration, a water soluble salt of the drug is dissolved in an isotonic salt solution and administered by the intravenous route. For oral administration, a pharmaceutically-acceptable salt of the drug is mixed with standard pharmaceutical excipients such as starch and loaded into capsules or made into tablets, each containing about 0.1 to about 100 mg of active drug. Dosage levels of from about 0.01–1000 mg/kg are effective in blocking $5HT_2$ receptors. Thus, the oral dosage would be administered 2–4 times per day, giving a daily dosage range of about 0.003 to about 10.0 mg/kg per day.

In order to demonstrate that the compounds of the invention have an extremely high affinity for $5HT_2$ receptors, apparent dissociation constants ($K_B$) as a measure of affinity for $5HT_2$ receptors, expressed as the negative logarithm, have been determined according to the following protocol.

Male Wistar rats (about 150–300 gram weight) were killed and their external jugular veins and thoracic aortas dissected free of connective tissue, cannulated in situ and placed in a modified Krebs' bicarbonate buffer in a suitable tissue bath. Two L-shaped 30-gauge stainless-steel hypodermic needles were inserted in each cannula and the dissected vessels gently pushed onto the needles. One needle was attached with thread to a stationary glass rod and the other to the transducer. [The procedure employed was that described by Hooker, Calkins and Fleisch, *Blood Vessels*, 14, 1, (1977) for use with circular smooth muscle preparations.]

The modified Krebs' bicarbonate buffer was composed of the following (concentrations in millimoles): sodium chloride, 118.2; potassium chloride, 4.6; calcium chloride dihydrate, 1.6; potassium dihydrogenphosphate, 1.2; magnesium sulfate, 1.2; dextrose, 10.0; sodium bicarbonate, 24.8; and water q.s. to 1000 g. The tissue baths were maintained at 37° C. and were aerated with 95% oxygen: 5% carbon dioxide (v:v). An initial optimum resting force of 1 g and 4 g was applied to the jugular vein and aorta, respectively. Isometric contractions were recorded as changes in grams of force on a Beckman Dynograph with Statham UC-3 transducers and microscale accessory attachment. Tissues were allowed to equilibrate 1 to 2 hours before exposure to drugs. Control responses to serotonin in the jugular vein and to norepinephrine in the aorta were obtained. The vessels were then incubated with appropriate concentrations of the test compound for one hour. Responses to serotonin or to norepinephrine were then repeated in the presence of the test compound. Contraction to serotonin was evaluated in the jugular vein since this tissue produces marked responses to serotonin in the absence of alpha receptors. See Cohen and Wiley, *J. Pharm. Exp. Ther.*, 205, 400 (1978). Alpha receptor antagonist activity was evaluated in the aorta.

Apparent antagonist dissociation constants were determined for each concentration of the test compound according to the following equation:

$$K_B = \frac{[B]}{[\text{dose ratio} - 1]}$$

wherein [B] is the concentration of the antagonist and the dose ratio is the $ED_{50}$ of the agonist in the presence of the antagonist divided by the control $ED_{50}$. These results are then expressed as the negative logarithm of $K_B$. The $-\log K_B$ values obtained for representative sensitive compounds of this invention and are given below in Table 1. In the Table, column I provides the Example Number of the compound evaluated in the screen; columns 2-6, the identity of the compound evaluated in the screen when taken with the structure provided; and column 7, the apparent dissociation constant for the test compound.

TABLE 1

Apparent Dissociation Constants for 5HT$_2$ Receptors

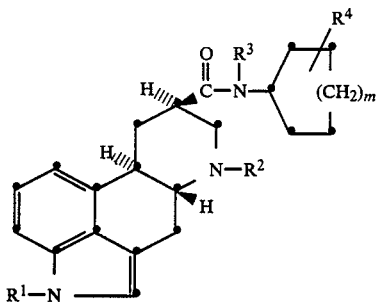

| Ex. | $R^1$ | $R^2$ | $R^3$ | $R^4$ | m | 5HT$_2$ $-\log K_B$ |
|---|---|---|---|---|---|---|
| 1 | CH(CH$_3$)$_2$ | CH$_3$ | H | H | 1 | 9.67 |
| 2 | CH(CH$_3$)$_2$ | CH$_3$ | CH$_3$ | H | 1 | 9.0 |
| 3 | CH(CH$_3$)$_2$ | (CH$_2$)$_2$CH$_3$ | H | H | 1 | 9.1 |
| 4 | CH(CH$_3$)$_2$ | CH$_3$ | H | cis 4-OCH$_3$ | 1 | 9.73 |
| 5 | CH(CH$_3$)$_2$ | CH$_3$ | H | trans 4-OCH$_3$ | 1 | 9.73 |
| 6 | CH$_3$ | CH$_3$ | H | cis 4-OCH$_3$ | 1 | 9.57 |
| 7 | CH$_2$CH$_3$ | CH$_3$ | H | cis 4-OCH$_3$ | 1 | 9.64 |
| 8 | CH$_3$ | CH$_3$ | H | H | 1 | 9.70 |
| 9 | CH(CH$_3$)$_2$ | CH$_3$ | H | H | 0 | 10.33 |
| 10 | CH$_2$CH$_3$ | CH$_3$ | H | H | 1 | 9.25 |
| 11 | CH(CH$_3$)$_2$ | CH$_3$ | H | trans 4-OH | 1 | 8.19 |
| 12 | CH(CH$_3$)$_2$ | CH$_3$ | H | H | 2 | 8.98 |
| 13 | CH(CH$_3$)$_2$ | CH$_3$ | H | 4-CH$_3$ | 1 | 8.19 |
| 14 | CH(CH$_3$)$_2$ | CH$_3$ | H | 2-OH | 1 | 10.56 |

The compounds of the present invention have also been found to have the ability to treat sexual dysfunction in mammals. As such, yet another embodiment of the present invention is a method for treating sexual dysfunction in mammals suffering from such dysfunction and in need of treatment comprising administering to said mammal a compound of the invention. For oral administration, preferably a pharmaceutically-acceptable salt of the drug is mixed with standard pharmaceutical excipients, such as starch, and loaded into capsules each containing about 0.1–15 mg of active drug. Dosage levels of from about 0.01–1000 mcg (micrograms)/kg have been found to be effective in improving sexual function, particularly in increasing male potency. The oral dosage forms would be administered 3-4 times per day, giving a daily dosage range of about 0.3 mcg/kg per day to about 400 mcg/kg per day.

The ability of the compounds of the present invention to affect sexual behavior in male animals was established by the following experiments.

Adult male rats of the Sprague-Dawley strain were used in these studies. The sexual behavior evaluations were conducted at 2-week intervals beginning at 6 months of age and ending at 12 months of age. During the initial screening process, the male rats of various levels of sexual performance were selected for compound testing. These performance levels included male rats that displayed no mounting behavior (Non-Maters); male rats that were able to mount but were unable to ejaculate during the test period (Non-Ejaculators); and male rats that were able to ejaculate during the test period. Prior to treatment with a drug solution, each male rat was required to have at least two consecutive vehicle tests with similar sexual performance. Following each compound testing, additional vehicle tests were performed. In an effort to eliminate behavioral responses with compound treatment that may be due to spontaneous changes in mating performance, a criterion of reversibility of behavioral response with subsequent vehicle treatment was employed Thus, a valid behavioral response to a drug treatment was arbitrarily set as a response that either did not change from the prior control response or was reversed in the subsequent control test with vehicle.

The mating tests were performed during the dark phase of the lighting cycle using red light illumination. Each behavioral test was initiated with the introduction of a receptive female rat into the arena and was terminated either 30 minutes later or immediately following the first postejaculatory mount. The indices of mating performance that were evaluated for the rats capable of ejaculation included mount latency (the time interval from the introduction of the female rat to the first mount); intromission latency (the time interval from the introduction of the female rat to the first intromission); ejaculatory latency (the time interval from intromission to ejaculation); postejaculatory interval (the time from ejaculation to the next mount); mount frequency (the total number of mounts with or without intromission prior to ejaculation); intromission frequency (the number of mounts with intromission prior to ejaculation); intromission efficiency (the intromission frequency divided by the mount frequency); copulatory rate (the number of mounts per minute); copulatory frequency (the number of mounts prior to ejaculation); and copulatory efficiency (the number of mounts with intromission divided by the total number of mounts).

Each male rat was given a solution containing either the vehicle alone in water or the compound of Example 1, (8β)-N-cyclohexyl-1-isopropyl-6-methylergoline-8-carboxamide, in the same vehicle. Vehicle was made of 1 mM (millimolar) acetic acid and 1 mM ascorbic acid.

The results of these studies are set forth below in Tables II–VII. In the Tables "N" is the number of animals used to generate the data, the average of which is provided. The specific description of the test performed is set forth in the heading of the Tables.

TABLE II

Effects of Example 1 on Copulatory Performance Of Male Rats - Subcutaneous Administration

| Dose (ng/kg) | Non-Maters | Non-Ejaculators |
|---|---|---|
| | Percent Responding | |
| 1 | 6.3 (1/16) | 11.1 (1/9) |
| 10 | 28.6 (4/14) | 45.0 (9/20) |
| 100 | 57.1 (8/14) | 54.5 (6/11) |
| 1000 | 58.3 (7/12) | 56.3 (9/16) |
| 10000 | 54.5 (6/11) | 61.1 (11/18) |

Numbers in parentheses indicate the fraction of responding rats

TABLE III

Effects of Example 1 on Copulatory Performance Of Male Rats - Subcutaneous Administration

| | Ejaculatory Latency | Postejaculatory Latency |
|---|---|---|
| Control | 602.6 ± 47.4 | 366.9 ± 15.6 |
| 0.01 mcg/kg | 530.4 ± 64.6 | 366.8 ± 19.8 |
| N = 14 | | |
| Control | 747.9 ± 61.8 | 367.1 ± 18.7 |
| 0.10 mcg/kg | 532.9 ± 58.0 | 355.9 ± 13.2 |
| N = 15 | * | |
| Control | 749.5 ± 59.1 | 371.2 ± 19.8 |
| 1.0 mcg/kg | 584.8 ± 89.4 | 357.3 ± 9.5 |
| N = 11 | * | |
| Control | 850.4 ± 99.2 | 368.3 ± 23.0 |
| 10.0 mcg/kg | 454.1 ± 78.4 | 333.9 ± 10.9 |
| N = 11 | * | |
| Control | 731.8 ± 44.5 | 373.3 ± 22.8 |
| 100.0 mcg/kg | 463.6 ± 46.6 | 325.6 ± 16.0 |
| N = 16 | * | |

Asterisk denotes statistically significant changes
Control values were obtained from the same rats 2 weeks earlier following vehicle administration
All injections were made 30 minutes prior to testing
Values for Ejaculatory Latency and Postejaculatory Latency are given in seconds

TABLE IV

Effects of Example 1 On Copulatory Performance Of Male Rats - Subcutaneous Administration

| | Mount Frequency | Copulatory Efficiency | Copulatory Rate |
|---|---|---|---|
| Control | 20.1 ± 2.4 | 0.59 ± 0.05 | 2.1 ± 0.2 |
| 0.01 mcg/kg | 21.4 ± 2.0 | 0.56 ± 0.03 | 2.4 ± 0.3 |
| N = 14 | | | |
| Control | 25.0 ± 2.3 | 0.38 ± 0.03 | 2.0 ± 0.2 |
| 0.10 mcg/kg | 22.9 ± 2.6 | 0.54 ± 0.04 | 2.7 ± 0.3 |
| N = 15 | | * | * |
| Control | 23.1 ± 2.4 | 0.53 ± 0.04 | 1.9 ± 0.2 |
| 1.00 mcg/kg | 21.4 ± 1.7 | 0.67 ± 0.03 | 2.4 ± 0.2 |
| N = 11 | | * | * |
| Control | 23.2 ± 2.1 | 0.49 ± 0.05 | 1.7 ± 0.2 |
| 10.0 mcg/kg | 18.5 ± 2.4 | 0.57 ± 0.04 | 2.6 ± 0.4 |
| N = 11 | | * | * |
| Control | 24.8 ± 2.3 | 0.49 ± 0.03 | 2.1 ± 0.2 |
| 100.0 mcg/kg | 21.3 ± 1.4 | 0.59 ± 0.04 | 2.9 ± 0.3 |
| N = 16 | | * | * |

Asterisk denotes statistically significant changes
Control values were obtained from the same animals 2 weeks earlier following vehicle administration
All injections were made 30 minutes prior to testing

TABLE V

Effects of Example 1 on Copulatory Performance Of Male Rats - Oral Administration

| | Ejaculatory Latency | Postejaculatory Latency |
|---|---|---|
| Control | 713.6 ± 58.1 | 358.5 ± 23.1 |
| 0.01 mcg/kg | 689.2 ± 91.2 | 370.2 ± 23.7 |
| N = 17 | * | |
| Control | 735.4 ± 51.9 | 381.9 ± 13.4 |
| 0.1 mcg/kg | 486.5 ± 70.8 | 313.4 ± 12.0 |
| N = 14 | * | * |
| Control | 646.3 ± 51.0 | 384.1 ± 23.5 |
| 1.0 mcg/kg | 415.9 ± 62.3 | 322.1 ± 15.3 |
| N = 8 | * | |
| Control | 731.0 ± 87.0 | 345.1 ± 20.3 |
| 10.0 mcg/kg | 434.2 ± 37.9 | 299.7 ± 15.1 |
| N = 12 | * | * |
| Control | 804.6 ± 73.5 | 417.9 ± 28.4 |
| 100.0 mcg/kg | 366.1 ± 52.2 | 350.6 ± 29.5 |
| N = 8 | * | |

*denotes statistically significant changes
All solutions were administered by gavage 90 minutes prior to testing.
Control responses were obtained from the same rats 2 weeks earlier following vehicle administration by gavage.

TABLE VI

Effects of Example 1 On Copulatory Performance Of Male Rats - Oral Administration

| | Mount Frequency | Copulatory Efficiency | Copulatory Rate |
|---|---|---|---|
| Control | 29.7 ± 2.9 | 0.43 ± 0.04 | 2.5 ± 0.2 |
| 0.01 mcg/kg | 27.5 ± 4.4 | 0.46 ± 0.05 | 2.3 ± 0.2 |
| N = 17 | * | | |
| Control | 19.4 ± 2.4 | 0.60 ± 0.05 | 1.7 ± 0.2 |
| 0.1 mcg/kg | 18.7 ± 2.1 | 0.60 ± 0.05 | 2.5 ± 0.4 |
| N = 14 | | | * |
| Control | 21.1 ± 3.9 | 0.59 ± 0.06 | 2.0 ± 0.4 |
| 1.0 mcg/kg | 16.8 ± 1.8 | 0.58 ± 0.04 | 2.7 ± 0.4 |
| N = 8 | * | | |
| Control | 25.9 ± 1.6 | 0.43 ± 0.03 | 2.2 ± 0.2 |
| 10.0 mcg/kg | 22.9 ± 1.2 | 0.49 ± 0.04 | 3.3 ± 0.3 |
| N = 12 | | | * |
| Control | 19.4 ± 1.7 | 0.51 ± 0.06 | 1.4 ± 0.1 |
| 100.0 mcg/kg | 14.4 ± 1.3 | 0.69 ± 0.04 | 2.6 ± 0.4 |
| N = 8 | * | * | * |

*denotes statistically significant changes.
Solutions were administered by gavage 90 minutes prior to testing.
Control values represent the responses of the same rates to vehicle P.O. administration 2 weeks prior to drug test.

TABLE VII

Effects of Example 1 On Copulatory Performance Of Male Rats Following Subcutaneous Administration Of Example 1 at 10 mcg/kg After Various Time Periods

| | Ejaculatory Latency | Postejaculatory Interval | Copulatory Rate |
|---|---|---|---|
| Control | 850.4 ± 99.2 | 368.3 ± 23.0 | 1.7 ± 0.2 |
| 0.5 hours | 454.1 ± 78.4 | 333.9 ± 10.9 | 2.6 ± 0.4 |
| N = 11 | * | | * |
| Control | 653.1 ± 61.7 | 349.5 ± 16.8 | 2.6 ± 0.2 |
| 8.0 hours | 402.3 ± 59.7 | 320.1 ± 17.0 | 3.9 ± 0.5 |
| N = 11 | * | * | * |
| Control | 815.5 ± 64.6 | 422.4 ± 25.5 | 2.0 ± 0.3 |
| 24.0 hours | 604.1 ± 68.4 | 391.7 ± 18.7 | 2.8 ± 0.4 |
| N = 15 | * | | * |
| Control | 591.0 ± 33.8 | 364.8 ± 27.8 | 2.4 ± 0.2 |
| 48.0 hours | 531.8 ± 60.6 | 365.4 ± 20.2 | 2.5 ± 0.2 |
| N = 11 | | * | * |

*denotes statistically significant changes
Units of measure: EL = seconds; PEI = seconds; CR = mounts/minute The compounds of the present invention are preferably formulated prior to administration. Therefore, yet another embodiment of the present invention is a pharmaceutical formulation comprising a compound of the invention and a pharmaceutically acceptable carrier, diluent or excipient therefor.

The present pharmaceutical formulations are prepared by known procedures using well known and readily available ingredients In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), ointments containing, for example, up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient by employing procedures well known in the art.

The compositions are preferably formulated in a unit dosage form, each dosage containing from about 5 to about 500 mg, more usually about 25 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The following formulation examples are illustrative only and are not intended to limit the scope of the invention in any way.

FORMULATION 1

Hard gelatin capsules are prepared using the following ingredients:

|  | Quantity (mg/capsule) |
| --- | --- |
| 8β-N-cyclohexyl-1-isopropyl-6-methyl-ergoline-8-carboxamide | 250 |
| starch, dried | 200 |
| magnesium stearate | 10 |
| Total | 460 mg |

The above ingredients are mixed and filled into hard gelatin capsules in 460 mg quantities.

FORMULATION 2

A tablet is prepared using the ingredients below:

|  | Quantity (mg/tablet) |
| --- | --- |
| (8β)-cis-N-(4-methoxycyclohexyl)-1-isopropyl-6-methylergoline-8-carboxamide | 250 |
| cellulose, microcrystalline | 400 |
| silicon dioxide, fumed | 10 |
| stearic acid | 5 |
| Total | 665 mg |

The components are blended and compressed to form tablets each weighing 665 mg.

FORMULATION 3

An aerosol solution is prepared containing the following components:

|  | Weight % |
| --- | --- |
| (8β)-trans-N-(4-methoxycyclohexyl)-1-isopropyl-6-methylergoline-8-carboxamide | 0.25 |
| ethanol | 29.75 |
| Propellant 22 (chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are than fitted to the container.

FORMULATION 4

Tablets each containing 60 mg of active ingredient are made as follows:

| (8β)-N-methyl-N-cyclohexyl-1-isopropyl-6-methylergoline-8-carboxamide | 60 mg |
| --- | --- |
| starch | 45 mg |
| microcrystalline cellulose | 35 mg |
| polyvinylpyrrolidone (as 10% solution in water) | 4 mg |
| sodium carboxymethyl starch | 4.5 mg |
| magnesium stearate | 0.5 mg |
| talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

FORMULATION 5

Capsules each containing 80 mg of medicament are made as follows:

| (8β)-N-cyclohexyl-1-isopropyl-6-n-propyl-ergoline-8-carboxamide maleate | 80 |
| --- | --- |
| starch | 59 mg |
| microcrystalline cellulose | 59 mg |

| | |
|---|---|
| magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

FORMULATION 6

Suppositories each containing 225 mg of active ingredient may be made as follows:

| | |
|---|---|
| (8β)-N-(4-hydroxycyclohexyl)-1-isopropyl-6-methylergoline-8-carboxamide | 225 mg |
| saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

FORMULATION 7

Suspensions each containing 50 mg of medicament per 5 ml dose are made as follows:

| | |
|---|---|
| (8β)-N-cycloheptyl-1-isopropyl-6-methylergoline-8-carboxamide | 50 mg |
| sodium carboxymethyl cellulose | 50 mg |
| syrup | 1.25 ml |
| benzoic acid solution | 0.10 ml |
| flavor | q.v. |
| color | q.v. |
| purified water to total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

FORMULATION 8

An intravenous formulation may be prepared as follows:

| | |
|---|---|
| (8β)-N-(4-methylcyclohexyl)-1-isopropyl-6-methylergoline-8-carboxamide hydrochloride | 100 mg |
| isotonic saline | 1000 ml |

The solution of the above ingredients is administered intravenously at a rate of 1 ml per minute to a subject in need of treatment for sexual dysfunction.

We claim:

1. A method of blocking 5HT$_2$ receptors which comprises administering to a mammal having an excess of serotonin centrally or peripherally a 5HT$_2$ blocking dose of a compound of the formula

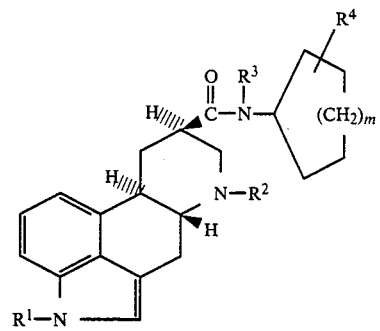

wherein:
$R^1$ is $C_1-C_4$ alkyl;
$R^2$ is allyl or $C_1-C_4$ straight chain alkyl;
$R^3$ is hydrogen of $C_1-C_4$ straight chain alkyl;
$R^4$ is hydrogen, $C_1-C_4$ alkyl, hydroxy or $C_1-C_4$ alkoxy;
m is 0, 1, 2 or 3;
provided when $R^1$ and $R^2$ are each methyl and $R^3$ and $R^4$ are each hydrogen, m may not be 0; and
the pharmaceutically acceptable acid addition salts thereof.

2. A method of claim 1 wherein $R^1$ is isopropyl.
3. A method of claim 2 wherein $R^2$ is methyl.
4. A method of claim 3 wherein $R^3$ is hydrogen.
5. A method of claim 4 wherein m is 1.
6. The method of claim 5 wherein the compound is (8β)-N-cyclohexyl-1-isopropyl-6-methylergoline-8-carboxamide.
7. A method of treating hypertension in mammals which comprises administering to a hypertensive mammal a hypotensive dose of a compound of the formula

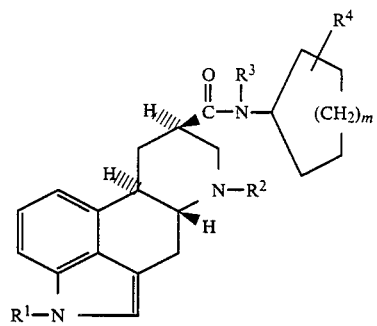

wherein:
$R^1$ is $C_1-C_4$ alkyl;
$R^2$ is allyl or $C_1-C_4$ straight chain alkyl;
$R^3$ is hydrogen or $C_1-C_4$ straight chain alkyl;
$R^4$ is hydrogen, $C_1-C_4$ alkyl, hydroxy on $C_1-C_4$ alkoxy;
m is 0, 1, 2 or 3;
provided when $R^1$ and $R^2$ are each methyl and $R^3$ and $R^4$ are each hydrogen, m may not be O; and
the pharmaceutically acceptable acid addition salts thereof.

8. A method of claim 7 wherein $R^1$ is isopropyl.
9. A method of claim 8 wherein $R^2$ is methyl.
10. A method of claim 9 wherein $R^3$ is hydrogen.
11. A method of claim 10 wherein n is 1.

12. The method of claim 11 wherein the compound is (8β)-N-cyclohexyl-1-isopropyl-6-methylergoline-8-carboxamide.

13. A method of treating migraine in mammals which comprises administering to a mammal suffering from migraine a migraine relieving dose of a compound of claim 1.

14. A method of claim 13 wherein $R^1$ is isopropyl.
15. A method of claim 14 wherein $R^2$ is methyl.
16. A method of claim 15 wherein $R^3$ is hydrogen.
17. A method of claim 16 wherein m is 1.
18. The method of claim 17 wherein the compound is (8β)-N-cyclohexyl-1-isopropyl-6-methylergoline-8-carboxamide.

19. A method of treating vasospasm in mammals which comprises administering to a mammal experiencing vasospasm a vasospasm relieving dose of a compound of the formula

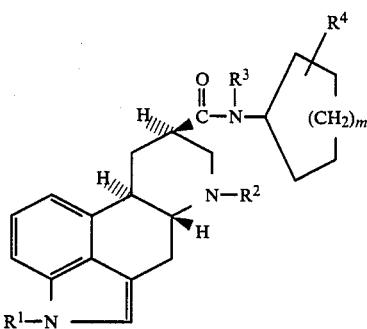

wherein:
$R^1$ is $C_1$-$C_4$ alkyl;
$R^2$ is allyl or $C_1$-$C_4$ straight chain alkyl;
$R^3$ is hydrogen or $C_1$-$C_4$ straight chain alkyl;
$R^4$ is hydrogen, $C_1$-$C_4$ alkyl, hydroxy or $C_1$-$C_4$ alkoxy;
m is 0, 1, 2 or 3;
provided when $R^1$ and $R^2$ are each methyl and $R^3$ and $R^4$ are each hydrogen, m may not be 0; and
the pharmaceutically acceptable acid addition salts thereof.

20. A method of claim 19 wherein $R^1$ is isopropyl.
21. A method of claim 20 wherein $R^2$ is methyl.
22. A method of claim 21 wherein $R^3$ is hydrogen.
23. A method of claim 22 wherein m is 1.
24. The method of claim 23 wherein the compound is (8β)-N-cyclohexyl-1-isopropyl-6-methylergoline-8-carboxamide.

25. A method of treating thrombosis in mammals which comprises administering to a mammal subject to thrombotic episodes a thrombosis alleviating dose of a compound of the formula

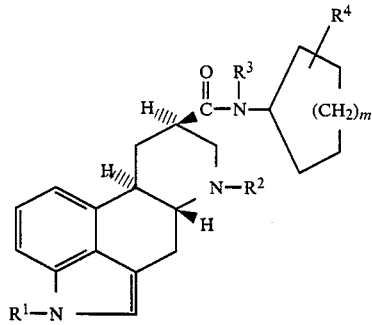

wherein:
$R^1$ is $C_1$-$C_4$ alkyl;
$R^2$ is allyl or $C_1$-$C_4$ straight chain alkyl;
$R^3$ is hydrogen or $C_1$-$C_4$ straight chain alkyl;
$R^4$ is hydrogen, $C_1$-$C_4$ alkyl, hydroxy or $C_1$-$C_4$ alkoxy;
m is 0, 1, 2 or 3;
provided when $R^1$ and $R^2$ are each methyl and $R^3$ and $R^4$ are each hydrogen, m may not be 0; and
the pharmaceutically acceptable acid addition salts thereof.

26. A method of claim 25 wherein $R^1$ is isopropyl.
27. A method of claim 26 wherein $R^2$ is methyl.
28. A method of claim 27 wherein $R^3$ is hydrogen.
29. A method of claim 28 wherein m is 1.
30. The method of claim 29 wherein the compound is (8β)-N-cyclohexyl-1-isopropyl-6-methylergoline-8-carboxamide.

31. A method of treating ischemia in mammals which comprises administering to a mammal suffering from ischemia an ischemia relieving dose of a compound of the formula

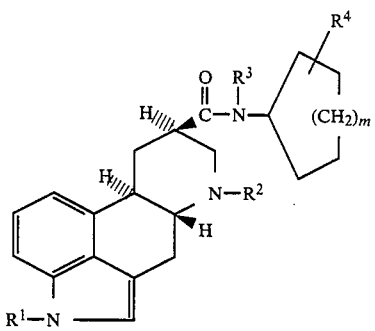

wherein:
$R^1$ is $C_1$-$C_4$ alkyl;
$R^2$ is allyl or $C_1$-$C_4$ straight chain alkyl;
$R^3$ is hydrogen or $C_1$-$C_4$ straight chain alkyl;
$R^4$ is hydrogen, $C_1$-$C_4$ alkyl, hydroxy or $C_1$-$C_4$ alkoxy;
m is 0, 1, 2 or 3;
provided when $R^1$ and $R^2$ are each methyl and $R^3$ and $R^4$ each hydrogen, m may not be 0; and
the pharmaceutically acceptable acid addition salts thereof.

32. A method of treating depression in mammals which comprises administering to a depressed mammal an antidepressant dose of a compound of the formula

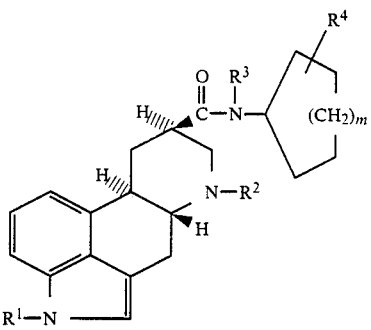

wherein:
R$^1$ is C$_1$-C$_4$ alkyl;
R$^2$ is allyl or C$_1$-C$_4$ straight chain alkyl;
R$^3$ is hydrogen of C$_1$-C$_4$ straight chain alkyl;
R$^4$ is hydrogen, C$_1$-C$_4$ alkyl, hydroxy or C$_1$-C$_4$ alkoxy;
m is 0, 1, 2 or 3;
provided when R$^1$ and R$^2$ are each methyl and R$^3$ and R$^4$ are each hydrogen, m may not be 0; and
the pharmaceutically acceptable acid addition salts thereof.

33. A method of treating anxiety in mammals comprising administering to a mammal suffering from anxiety an antianxiety dose of a compound the formula

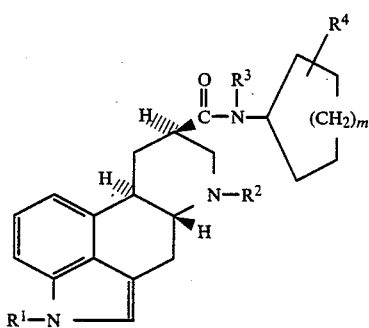

wherein:
R$^1$ is C$_1$-C$_4$ alkyl;
R$^2$ is allyl or C$_1$-C$_4$ straight chain alkyl;
R$^3$ is hydrogen or C$_1$-C$_4$ straight chain alkyl;
R$^4$ is hydrogen, C$_1$-C$_4$ alkyl, hydroxy or C$_1$-C$_4$ alkoxy;
m is 0, 1, 2 or 3;
provided when R$^1$ and R$^2$ are each methyl and R$^3$ and R$^4$ each hydrogen, m may not be 0; and
the pharmaceutically acceptable acid addition salts thereof.

34. A method of treating sleep disorders in mammals comprising administering to a mammal experiencing sleep disorders a sleep disorder relieving dose of a compound of the formula wherein:
R$^1$ is C$_1$-C$_4$ alkyl;
R$^2$ is allyl or C$_1$-C$_4$ straight chain alkyl;
R$^3$ is hydrogen or C$_1$-C$_4$ straight chain alkyl;
R$^4$ is hydrogen, C$_1$-C$_4$ alkyl, hydroxy or C$_1$-C$_4$ alkoxy;
m is 0, 1, 2 or 3;
providing when R$^1$ and R$^2$ are each methyl and R$^3$ and R$^4$ are each hydrogen, m may not be 0; and
the pharmaceutically acceptable acid addition salts thereof.

35. A method of claim 4 wherein m is 0.
36. A method of claim 10 wherein R$_4$ is hydroxy.
37. A method of claim 10 wherein m is 0.
38. A method of claim 10 wherein R$_4$ is hydroxy.
39. A method of claim 15 wherein m is 0.
40. A method of claim 15 wherein R$_4$ is hydroxy.
41. A method of claim 22 wherein m is 0.
42. A method of claim 22 wherein R$_4$ is hydroxy.
43. A method of claim 28 wherein m is 0.
44. A method of claim 28 wherein R$_4$ is hydroxy.

* * * * *

UNITED STATES PATENT AND TRADEMARK OFFICE
CERTIFICATE OF CORRECTION

PATENT NO. : 4,931,447

DATED : June 5, 1990

INVENTOR(S) : William L. Garbrecht et al.

It is certified that error appears in the above-identified patent and that said Letters Patent is hereby corrected as shown below:

On the title page, under item [19], change "Foreman et al" to read
-- Garbrecht et al --.

Item [75] should read: Inventors: William L. Garbrecht; Gifford P. Marzoni: both of Indianapolis; Kathleen R. Whitten, Zionsville, all of Indiana.

Column 3, line 59, change "(8≠)-N-(4-methoxycyclohexyl)-" to
-- (8β)-N-(4-methoxycyclohexyl)- --.

Column 7, line 48, change "(8β)-6-ergoline-8-carboxylic acid " to
-- (8β)-ergoline-8-carboxylic acid --.

Column 13, line 11, change "methylergoline-8-carboxamide" to
-- 6-methylergoline-8-carboxamide --.

Column 13, line 18, change "72°C." to -- 75°C --.

Column 26, line 33 (Claim 36), change "claim 10" to --claim 4--.

Signed and Sealed this

Sixth Day of August, 1991

*Attest:*

HARRY F. MANBECK, JR.

*Attesting Officer*  *Commissioner of Patents and Trademarks*

UNITED STATES PATENT AND TRADEMARK OFFICE
CERTIFICATE OF CORRECTION

PATENT NO. : 4,931,447
DATED : June 5, 1990
INVENTOR(S) : William L. Garbrecht et al.

Page 1 of 2

It is certified that error appears in the above-identified patent and that said Letters Patent is hereby corrected as shown below:

On the title page item [19], should read
-- Garbrecht et al --.

Item [75] should read: Inventors: William L. Garbrecht; Gifford P. Marzoni; both of Indianapolis; Kathleen R. Whitten, Zionsville, all of Indiana.

Column 3, line 59, change "(8≠)-N-(4-methoxycyclohexyl)-" to
-- (8β)-N-(4-methoxycyclohexyl)- --.

Column 7, line 48, change "(8β)-6-ergoline-8-carboxylic acid " to
-- (8β)-ergoline-8-carboxylic acid --.

Column 13, line 11, change "methylergoline-8-carboxamide" to
-- 6-methylergoline-8-carboxamide --.

Column 13, line 18, change "72°C." to -- 75°C --.

Column 23, line 7, change "Claim 1." to -- the formula

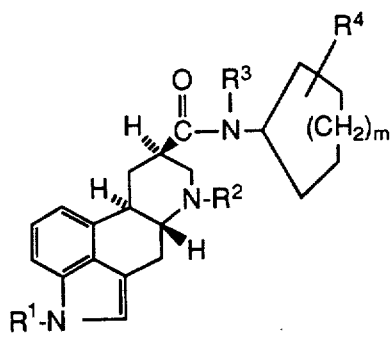

UNITED STATES PATENT AND TRADEMARK OFFICE
CERTIFICATE OF CORRECTION

PATENT NO. : 4,931,447
DATED : June 5, 1990
INVENTOR(S) : William L. Garbrecht et al.   Page 2 of 2

It is certified that error appears in the above-identified patent and that said Letters Patent is hereby corrected as shown below:

wherein:

$R^1$ is $C_1$-$C_4$ alkyl;
$R^2$ is allyl or $C_1$-$C_4$ straight chain alkyl;
$R^3$ is hydrogen or $C_1$-$C_4$ straight chain alkyl;
$R^4$ is hydrogen, $C_1$-$C_4$ alkyl, hydroxy or $C_1$-$C_4$ alkoxy;
m is 0, 1, 2 or 3;
provided when $R^1$ and $R^2$ are each methyl and $R^3$ and $R^4$ each hydrogen, m may not be 0; and the pharmaceutically acceptable acid addition salts thereof.--

Column 26, line 33 (Claim 36), change "claim 10" to -- claim 4 --.

Signed and Sealed this

Twenty-second Day of December, 1992

Attest:

DOUGLAS B. COMER

Attesting Officer    Acting Commissioner of Patents and Trademarks